US007007540B2

(12) United States Patent
Koland et al.

(10) Patent No.: US 7,007,540 B2
(45) Date of Patent: *Mar. 7, 2006

(54) METHODS AND APPARATUS FOR CONDUCTING HIGH G-FORCE TESTING

(75) Inventors: Lisa P. Koland, Minneapolis, MN (US); Owen D. Grossman, Golden Valley, MN (US)

(73) Assignee: Honeywell International Inc., Morristown, NJ (US)

( * ) Notice: Subject to any disclaimer, the term of this patent is extended or adjusted under 35 U.S.C. 154(b) by 21 days.

This patent is subject to a terminal disclaimer.

(21) Appl. No.: 10/699,303

(22) Filed: Oct. 31, 2003

(65) Prior Publication Data

US 2005/0092060 A1    May 5, 2005

(51) Int. Cl.
*G01M 7/00* (2006.01)
(52) U.S. Cl. .................................... 73/12.09
(58) Field of Classification Search ............... 73/12.01, 73/12.04, 12.07, 12.09
See application file for complete search history.

(56) References Cited

U.S. PATENT DOCUMENTS

| | | | | |
|---|---|---|---|---|
| 3,589,682 A | * | 6/1971 | Dickey | ......................... 256/59 |
| 4,426,683 A | | 1/1984 | Kissell | |
| 4,433,570 A | | 2/1984 | Brown et al. | |
| 4,884,456 A | * | 12/1989 | Meline et al. | ................. 73/826 |
| 5,341,943 A | * | 8/1994 | Fraser | .......................... 211/40 |
| 5,487,298 A | * | 1/1996 | Davis et al. | ................ 73/12.05 |
| 5,677,494 A | | 10/1997 | Keener et al. | |
| 5,744,947 A | * | 4/1998 | Jacobsen et al. | ............. 324/106 |
| 6,408,205 B1 | | 6/2002 | Renirie et al. | |
| 6,553,807 B1 | | 4/2003 | Luk et al. | |
| 6,655,190 B1 | * | 12/2003 | Grossman et al. | .......... 73/12.07 |
| 2003/0101794 A1 | | 6/2003 | Grossman et al. | |

OTHER PUBLICATIONS

International Search Report and the Written Opinion of the International Searching Authority, or the Declaration, dated Apr. 13, 2005; 12 pgs.

* cited by examiner

*Primary Examiner*—Max Noori
(74) *Attorney, Agent, or Firm*—Andrew Abeyta, Esq.; Armstrong Teasdale LLP

(57) ABSTRACT

A high-g shock-producing device for testing a sample specimen is described which includes a beam and a shock column. The beam is of predetermined length and has at least one end substantially rigidly fixed with the specimen mounted thereon at a position remote from the one end. The shock column is positioned to apply a force causing said beam to bend in a direction transverse to the length. The column is configured to have a buckling failure when exposed to a pressure which is sufficient to bend the beam an amount to provide the desired high-g force to the specimen. The buckling failure causes the force to be suddenly removed from the beam so as to release the beam and produce the high-g shock on the specimen.

25 Claims, 4 Drawing Sheets

METHODS AND APPARATUS FOR CONDUCTING HIGH G-FORCE TESTING

BACKGROUND OF THE INVENTION

This invention relates generally to shock testing, and more particularly to an apparatus and method for subjecting a test specimen to a high-g shock in the laboratory to simulate the conditions the specimen might encounter in an intended use.

A test specimen, for example, an accelerometer, may be tested under substantially identical conditions as will be encountered in actual use. One such example is a gun launch test. However, the cost of transporting the specimen to a gun launch test facility and performance of the gun launch testing is very high. In addition, typically it is feasible to conduct only one or two gun launch tests per day. As such, it is economically and logistically beneficial to perform as much laboratory testing as possible, so as to minimize expense and increase convenience, so that many more tests per day can be performed.

One such laboratory testing apparatus is a bench top high-g shock tester. The shock tester uses a ceramic column to load a beam that is rigidly supported at each end. In one known test setup, the ceramic column is shot out, utilizing a projectile, to release the beam fast enough to cause the beam to resonate and apply high-g loads to any samples attached to the beam. In another known test setup, the ceramic column was replaced with an explosive bolt, which also released the beam fast enough to allow it to resonate.

Typically aluminum is utilized for the beam due to its low cost and ease of machining. However, some high-g load testing is performed with titanium beams, which can withstand a much higher loading level than the ceramic columns can withstand. The higher loading level also results in an instability of the ceramic columns.

BRIEF SUMMARY OF THE INVENTION

In one aspect, a high-g shock-producing device for testing a sample specimen is provided. The device comprises a beam of predetermined length having at least one end substantially rigidly fixed with the specimen mounted thereon at a position remote from the one end and a shock column. The shock column is positioned to apply a force causing the beam to bend in a direction transverse to its length. The column is further configured to have a buckling failure when exposed to a pressure which is sufficient to bend the beam an amount to provide the desired high-g force to the specimen. The buckling failure of the column causes the force to be suddenly removed from the beam so as to release the beam and produce the high-g shock on the specimen.

In another aspect, a method of suddenly releasing a beam of a high-g force testing apparatus is provided. The method comprises configuring a shock column with a buckling failure point, the buckling failure point being at a pressure, inserting the shock column between a beam rigidly mounted at least at one end and a pressure producing device, and applying a pressure to the shock column to bend the beam to a desired point, the pressure needed to bend the beam to the desired point being equal to the buckling failure point pressure of the shock column.

In still another aspect, a shock column for a high-g tester is provided. The shock column comprises a top cap, a bottom cap, and a column portion extending between the top cap and the bottom cap. The column portion is configured to buckle when a specific pressure is applied between the top cap and the bottom cap.

In yet another aspect, a high-g shock producing device for testing a specimen is provided, The high-g shock producing device comprises a beam having a first end and a second end, and capable of flexing without permanent deformation, rigidly mounted at the ends, and a fastener for mounting the specimen atop the I-beam proximate the center thereof. The device further comprises a shock column comprising a top cap, a bottom cap, and a column portion extending therebetween, and positioned such that the top cap bears against the beam. The shock column portion comprises a feature which causes the column portion to buckle at a specified pressure. The device also comprises a hydraulic ram positioned to produce a directed force on the bottom cap of the column to cause the beam to bend to a position where the pressure is sufficient to cause the column portion to buckle. The buckling of the column portion causes removal of the directed force thereby allowing the beam to suddenly unbend and apply a g-force to the specimen.

DETAILED DESCRIPTION OF THE INVENTION

Figure 1:
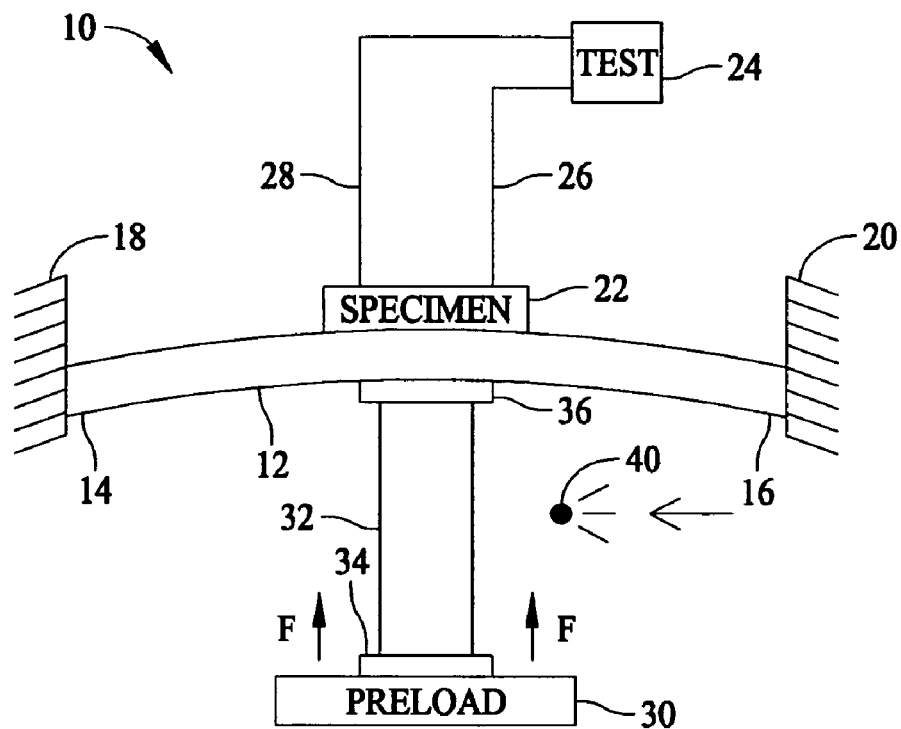
FIG. 1 is an illustration of a high-g tester.

FIG. 1 illustrates a high-g shock tester 10. Tester 10 includes a beam 12 of high strength material, for example, aluminum or titanium, which in one embodiment, is shaped in the form of an I-beam. Beam 12 is shown rigidly connected at both ends 14, 16 to a solid structure shown by mounting portions 18 and 20.

In one embodiment, high strength aluminum is utilized as a material for beam 12, because of its high yield point (i.e., its ability to flex without permanent deformation), its low cost, and the ease with which it may be machined. Alternately, titanium and other high-yield-point materials may be used but generally at a higher cost. In one embodiment, an I-beam configuration is used for beam 12 to provide strength and store energy with as little weight as possible. In general, the greater the weight, the less amplitude of acceleration results.

A specimen 22 to be tested, which may be any of a variety of devices such as a printed circuit, an accelerometer, or a gyroscope, is fastened utilizing a fastener (not shown) to an approximate middle of beam 12 in preparation of the high-g test of specimen 22. Specimen 22 is connected to a test apparatus 24 by wires 26 and 28, or another method of connection, to record or monitor the effects of the high-g test.

A force, denoted in FIG. 1 as F, from pre-load producing device 30, for example, a hydraulic ram or another device capable of providing such a force, is shown as connected to beam 12 by a member 32 to produce an upwardly directed force as shown by the force arrows. Other embodiments are contemplated, for example, where device 30 and member 32 direct a downward force onto beam 12. Member 32 is preferably a frangible material with high compression strength, such as a ceramic, to allow sudden fracture. In another embodiment member 32 is an explosive bolt, which an operator can activate when a specific pressure onto beam 12 is attained.

In one embodiment, member 32 is provided with protective ends 34 and 36 to apply the force over a larger area, to help prevent the formation of indentations in beam 12. As the force is applied, beam 12 is bent upwardly, as shown, by an amount which provides the g-force needed to perform the high-g test, but in no event past the yield point of beam 12.

Once the beam is bent the amount needed to perform the high-g test, a projectile 40 or other shattering device is utilized to break or shatter member 32, as shown by the directional arrow behind projectile 40. Beam 12 is then suddenly allowed to spring back downwardly, producing the high-g shock wave that subsequently is applied to specimen 22. At such time, beam 12 is sometimes said to be resonating, or oscillating. Utilization of an explosive bolt results in a similar motion of beam 12 upon activation of the bolt.

Figure 2:
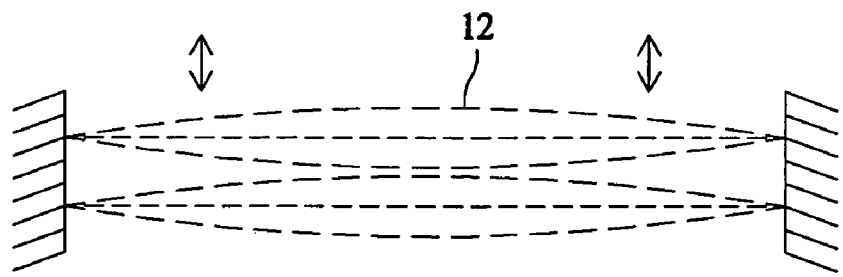
FIG. 2 illustrates oscillations of a beam of the high-g tester of FIG. 1 after removal of the column under the beam.

The oscillating action of beam 12 is depicted in FIG. 2. Although specimen 22 is not shown, it is understood that when specimen 22 is mounted on beam 12, specimen 22 is moving down and up with beam 12 until beam 12 quickly damps to a standstill, as does specimen 22. The high-g force, the maximum of which occurs during the first full cycle, is in the form of a damped sinusoid. If it was desirable to change the damping characteristics of tester 10, a damping member (not shown), for example, a dash pot, might be attached to beam 12. Projectile 40 or shattering device may be relatively small, and may be propelled by a pneumatic device and a relatively short coiled tube (not shown). Since the projectile does not impart the shock wave to the bar, its size and speed need only be great enough to shatter member 32. The application of a high-g force requires a relatively sudden release of beam 12, and the magnitude of the force may be adjusted using different amounts of bending for various requirements dictated by the specimen 22. Specimen 22 is shown attached near a center of beam 12 so that the g-force is directed primarily upwardly, and secondary g-forces in other directions are minimized. This is especially desirable for testing inertial devices such as gyroscopes and accelerometers.

Figure 3:
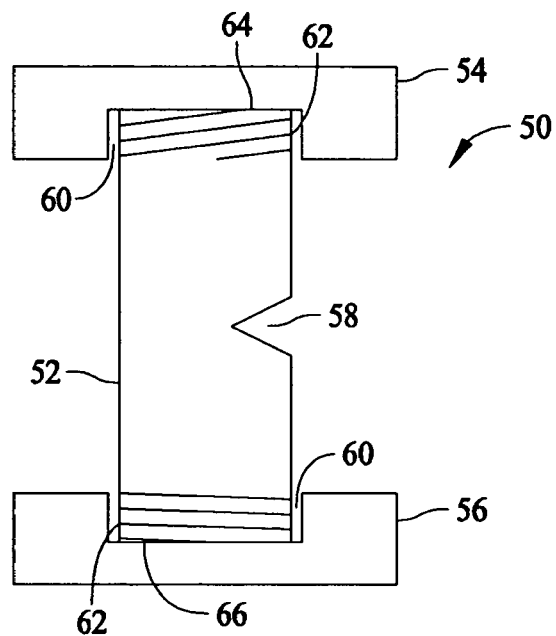
FIG. 3 is an illustration of a column calibrated to withstand a specific load pressure.

However, utilizing a projectile 40 has drawbacks, for example, the testing area should include safety precautions as any projectile should be considered as having an element of danger involved. In addition, when beam 12 is made from titanium, a higher load must be placed on the beam in order for it to flex as described above. The higher loading requirements sometimes cannot be met by ceramic members 32 as currently configured, nor by known explosive bolts. FIG. 3 illustrates a shock column 50 which is configured to meet the high loading requirements associated with titanium beams. Column 50 has improved stability over columns 32 (shown in FIG. 1).

As described below, column 50 incorporates features which allow columns 50 to be calibrated to withstand a specific load pressure. The load pressure on a titanium beam directly correlates to shock level applied to a specimen. Column 50 includes a column portion 52, a top cap 54, and a bottom cap 56. Column portion 52 includes a notch 58 formed therein which causes a buckling failure of column portion 52, and therefore column 50, and initiates oscillations of a beam at a specific load pressure. The buckling failure of column portion 52 can also eliminate the need to shoot out the ceramic column from under the loaded beam with a projectile as described above.

As different test specimens are tested at different and various shock levels, a size and depth of notch 58 can be adjusted at manufacture to provide the buckling failure at specific load pressures. In a preferred embodiment, column portion 52 is configured with notch 58 near a center of the span of column portion 52 to a depth calculated to correspond to buckling failure at a specific load level. Top cap 54 and bottom cap 56 are, in alternative embodiments, snug-fitting, threaded, made from a metal, and include a recess 60 into which ends 54 and 56 of column portion 52 are inserted. Utilization of top cap 54 and bottom cap 56 increases vertical stability of column 50 under a load.

Top cap 54 and bottom cap 56 are shown as having threads 62 which screw onto threaded end portions 64 and 66, respectively, of column portion 52. In other embodiments, top cap 54 and bottom cap 56 are configured with deformable, vertical or horizontal ridges, in place of threads, which are press fit onto end portions 64 and 66. The vertical and horizontal ridges provide a tight fit between column portion 52 and top cap 54 and bottom cap 56. Deformable vertical or horizontal ridges, also provide an amount of vertical stability for column 50 as a load is applied to beam 12. For example, the ridges (or threads in the threaded embodiment) are somewhat malleable under the stresses applied to bend a beam, and act to absorb at least a portion of any sideways forces encountered by column 50.

Figure 4:
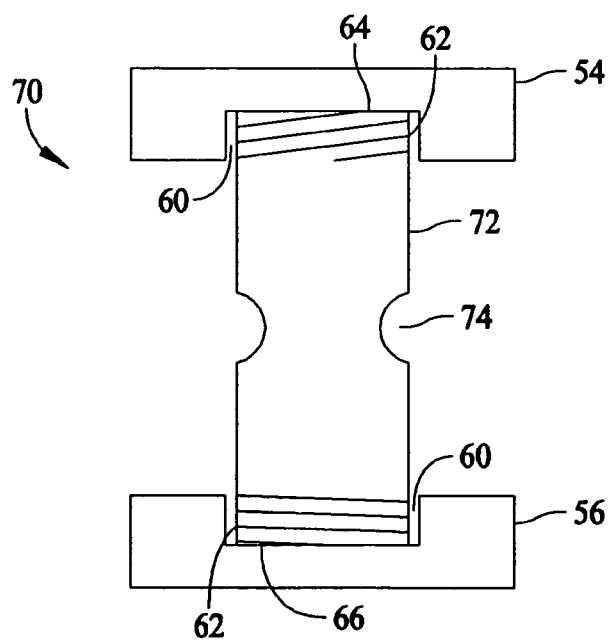
FIG. 4 is an illustration of another column configuration calibrated to withstand a specific load pressure.

FIG. 4 illustrates another embodiment of a shock column 70 which is configured to provide a buckling failure at specific load pressures. Specific components of column 70 which are the same as those described for column 50 (shown in FIG. 3) have the same reference numerals. Column 70 includes a column portion 72 which has a reduced cross-section portion 74. Reduced cross-section portion 74, when under the load of forcing a beam to bend, for example, beam 12 (shown in FIG. 1) causes column portion 72 to have a buckling failure when a specific load is reached. Reduced cross-section portions can be made longer, or deeper during manufacture of column portion 72 to provide buckling failures at various load pressures.

Figure 5:
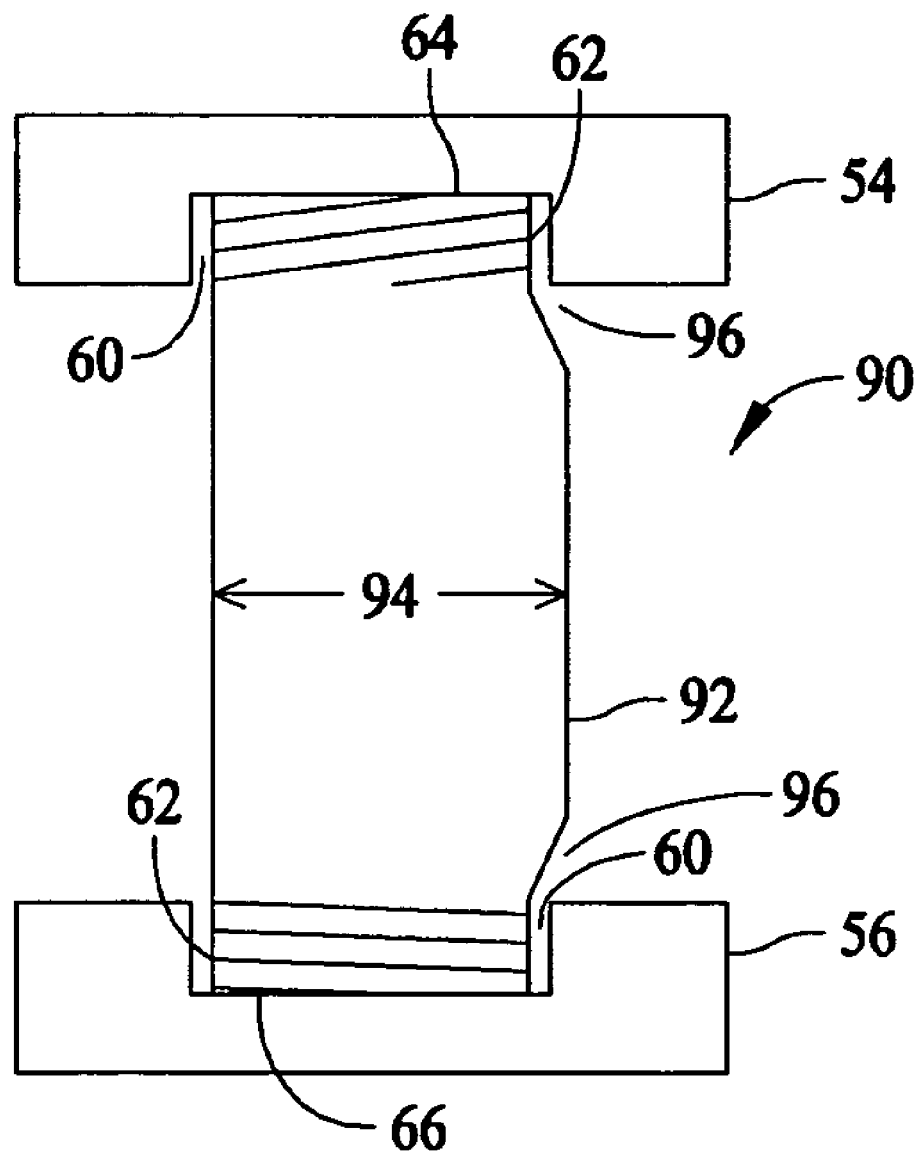
FIG. 5 is an illustration of a third column configuration calibrated to withstand a specific load pressure.

FIG. 5 illustrates still another shock column 90 which is configured to buckle under load pressures. Specific components of column 90 which are the same as those described for column 50 (shown in FIG. 3) have the same reference numerals. Column 90 includes a column portion 92 which has an enlarged cross-section 94 which is greater in diameter than threaded end portions 64 and 66. The configuration of enlarged cross-section 94 as shown in FIG. 5 results in a notch portion 96 near each of top cap 54 and bottom cap 56. Notch portions 96 are a stress point when column 90 is utilized to apply pressure to a beam, as described above, and result in a buckling failure at a specific load level. Enlarged cross-section 94, and notch section 96 can be configured in different sizes at manufacture of column 92, to provide failures at different load levels.

Figure 6:
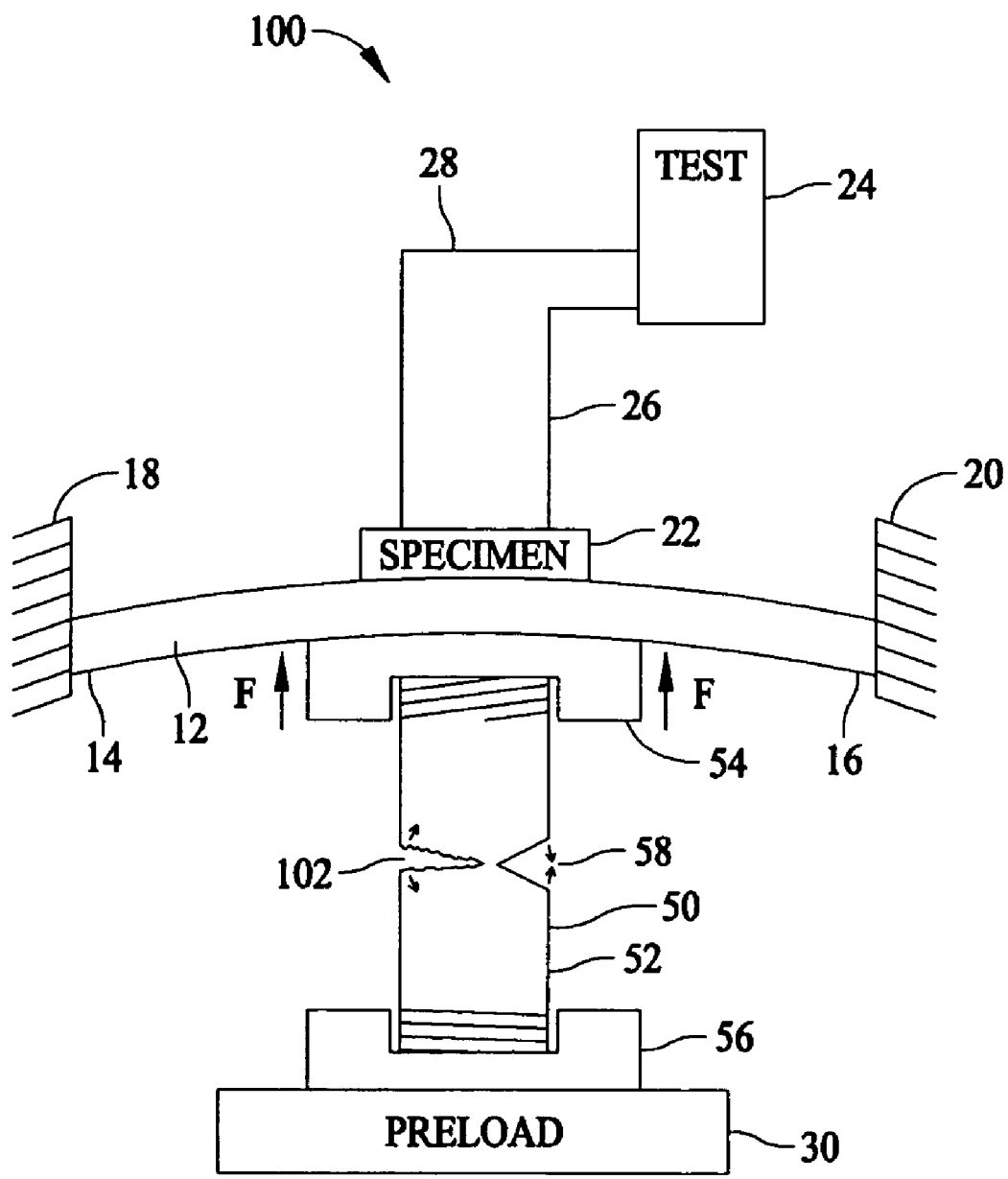
FIG. 6 is an illustration of a high-g load tester which utilizes the calibrated column of FIG. 3.

FIG. 6 illustrates a high-g load tester 100 which utilizes shock column 50, which is described in detail with respect to FIG. 3. Specific components of high-g load tester 100 which are the same as those components described for high-g load tester 10 (shown in FIG. 1) as shown utilizing the same reference numerals.

Load producing device 30 applies a force to beam 12 through shock column 50 to produce an upwardly directed force as shown by the force arrows. As the force is applied, beam 12 is bent upwardly, as shown, by an amount which provides the g-force needed to perform the high-g test. As the force applied by load producing device 30 increases, to the point needed to eventually provide the correct amount of g-force to specimen 22, the presence of notch 58 within column portion 52 of column 50 causes a fissure 102 to begin to develop in column portion 52. As fissure 102 develops across column 52, column portion 52 reaches a breaking point and separates, falling away from load producing device 30 and beam 12, allowing beam 12 to oscillate and apply the desired g-force to specimen 22.

Using shock columns 50, 70, and 90 increases reliability of high-g testing methods as controlling a buckling failure of such columns provides an increased repeatability of the high-g test methods herein described. Further, utilization of shock columns 50, 70, and 90 create a known and predictable failure mode, eliminate one step as compared to the known testing process (firing of a projectile), and increase the safety of the test process by removing an air-pressure propelled projectile from the procedure. In addition, utilization of top cap 54 and bottom cap 56 with deformable ridges or threads which are press fit onto a column portion allow a column assembly to absorb some of the sideways forces such a test setup might experience if a bottom surface of beam 12 or a top surface of load producing device 30 are not exactly parallel to one another.

While the invention has been described in terms of various specific embodiments, those skilled in the art will recognize that the invention can be practiced with modification within the spirit and scope of the claims.

What is claimed is:

1. A mechanical shock producing device for testing a sample specimen compnsing:
   a beam having a predetermined length and a first end and a second end, at least one of said first beam end and said second beam end having a substantially rigidly fixed position, with the specimen mounted on said beam at a position separated by a distance from the fixed position; and
   a shock column positioned to apply a force to said beam, the force causing said beam to bend in a direction transverse to the length, said column comprising a buckling failure formed therein, said buckling failure configured to cause said column to buckle when a specific force is applied to said beam through said column.

2. A mechanical shock-producing device according to claim 1 wherein said column comprises:
   a top cap;
   a bottom cap; and
   a column portion extending between said top cap and said bottom cap, said column portion comprising said buckling failure.

3. A mechanical shock-producing device according to claim 2 wherein said top cap, said bottom cap, and said column portion comprise threaded end portions, said top cap and said bottom cap configured to thread onto the threaded portion of said column portion.

4. A mechanical shock-producing device according to claim 2 wherein said top cap and said bottom cap comprise deformable ridges within a recess therein, said deformable ridges utilized in press fitting said top cap and said bottom cap to said column portion.

5. A mechanical shock-producing device according to claim 2 wherein said buckling failure comprises a notch formed near a center of the length of said column portion, said notch sized to cause said column portion to fail when a specific force is applied through said column portion.

6. A mechanical shock-producing device according to claim 2 wherein said buckling failure comprises a reduced cross-section formed near a center of the length of said column portion, said reduced cross-section sized to cause said column portion to fail when a specific force is applied through said column portion.

7. A mechanical shock-producing device according to claim 2 wherein said column portion comprises:
   end portions; and
   an enlarged cross-section extending between said end portions, said end portions and said enlarged cross-section forming notches where said end portions extend into said top cap and said bottom cap, said enlarged cross-section sized to cause said column portion to fail when a specific force is applied through said column portion.

8. A mechanical shock-producing device according to claim 2 wherein said column portion comprises a ceramic material.

9. A mechanical shock-producing device according to claim 2 wherein said beam comprises at least one of aluminum and titanium.

10. A mechanical shock-producing device according to claim 2 wherein said beam comprises an I-beam configuration.

11. A mechanical shock-producing device according to claim 2 wherein said top cap and said bottom cap comprise a metal.

12. A method for releasing a beam of a mechanical force testing apparatus, said method comprising:
    selecting a shock column with a buckling failure point, the buckling failure point being at a pressure;
    inserting the shock column between a beam rigidly mounted at least at one end and a pressure producing device; and
    applying a pressure through the shock column to bend the beam to a desired point, the pressure needed to bend the beam to the desired point being equal to the buckling failure point pressure of the shock column.

13. A method according to claim 12 wherein selecting a shock column with a buckling failure point comprises selecting the shock column with a notch formed near a center of the length of the shock column, the notch sized to provide the buckling failure at a pressure equal to the pressure needed to bend the beam to the desired point.

14. A method according to claim 12 wherein selecting a shock column with a buckling failure point comprises selecting the shock column with a reduced cross-section formed near a center of the length of the shock column, the reduced cross-section sized to provide the buckling failure at a pressure equal to the pressure needed to bend the beam to the desired point.

15. A method according to claim 12 wherein selecting a shock column with a buckling failure point comprises selecting the shock column with an enlarged cross-section extending between end portions of the shock column, the end portions and enlarged cross-section forming notches where the end portions extend into a top cap and a bottom cap, said enlarged cross-section sized to provide the buckling failure at a pressure equal to the pressure needed to bend the beam to the desired point.

16. A shock column for a mechanical testing device comprising:
    a top cap;
    a bottom cap; and
    a column portion extending between said top cap and said bottom cap, said column portion comprising a buckling failure formed therein, said buckling failure configured to cause said column to buckle when a specific pressure is applied between said top cap and said bottom cap.

17. A shock column according to claim 16 wherein said buckling failure comprises a notch formed near a center of the length of said column portion, said notch sized to cause said column portion to buckle at a specific pressure.

18. A shock column according to claim 16 wherein said buckling failure comprises a reduced cross-section formed near a center of the length of said column portion, said reduced cross-section sized to cause said column portion to buckle at a specific pressure.

19. A shock column according to claim 16 wherein said buckling failure comprises:

end portions; and an enlarged cross-section extending between said end portions, said end portions and said enlarged cross-section forming notches where said end portions extend into said top cap and said bottom cap, said enlarged cross-section sized to cause said column portion to buckle at a specific pressure.

20. A shock column according to claim 16 wherein said top cap, said bottom cap, and said column portion comprise threaded end portions, said top cap and said bottom cap threading onto said threaded portion of said column portion.

21. A shock column according to claim 16 wherein said top cap and said bottom cap comprise deformable ridges within a recess therein, said deformable ridges utilized in press fitting said top cap and said bottom cap to said column portion.

22. A mechanical shock producing device for testing a specimen comprising:

a beam having a first end and a second end, and capable of flexing, said beam rigidly mounted at said first end and said second end;

a fastener for mounting the specimen atop said on said beam proximate the center thereof;

a shock column comprising a top cap, a bottom cap, and a column portion extending therebetween, and positioned such that said top cap bears is against said beam, said column portion comprising a feature which causes said column portion configured to buckle at a specified pressure; and a hydraulic ram positioned to produce an upwardly directed force on said bottom cap of said column to cause said beam to bend to a position where the pressure is sufficient to cause said column portion to buckle, the buckling causing removal of the upwardly directed force thereby allowing said beam to suddenly unbend and apply a g force return to an unbent position thereby applying a mechanical force to the specimen.

23. A high-g shock producing device according to claim 22 wherein said top cap bears against is positioned near an approximate center of said beam.

24. A high-g shock producing device according to claim 23 wherein said beam comprises an I-beam.

25. A mechanical shock-producing device according to claim 1 wherein the specific force applied to said beam to initiate said buckling failure is equal to a force needed to bend said beam an amount to result in application of the desired mechanical force to the specimen.

* * * * *